United States Patent [19]
Wilson et al.

[11] Patent Number: 4,877,802
[45] Date of Patent: Oct. 31, 1989

[54] THIAZOLE DERIVATIVES

[75] Inventors: John R. H. Wilson, Rainham; Ernest Haddock, Sheerness, both of England

[73] Assignee: Shell Internationale Research Maatschappij B.V., The Hague, Netherlands

[21] Appl. No.: 199,430

[22] Filed: May 27, 1988

[30] Foreign Application Priority Data

Jun. 25, 1987 [GB] United Kingdom ............... 8714920

[51] Int. Cl.$^4$ ............... C07D 277/56; A01N 43/78
[52] U.S. Cl. ............... 514/365; 514/369; 514/370; 514/236.8; 540/133; 548/188; 548/194; 548/200
[58] Field of Search ............... 548/200, 188, 194; 540/133; 514/365, 369, 370, 230

[56] References Cited

U.S. PATENT DOCUMENTS

| 3,725,427 | 4/1973 | Harrison | 548/200 |
| 4,027,030 | 5/1977 | Poitteven | 548/200 |
| 4,427,688 | 1/1984 | Rentzea et al. | 514/361 |

FOREIGN PATENT DOCUMENTS 73973  3/1983  European Pat. Off. ............ 514/361

Primary Examiner—Robert Gerstl

[57] ABSTRACT

The invention provides thiazole derivatives of gener formula I;

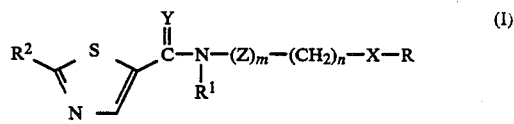

or an acid-addition salt or metal salt complex thereof, in which R represents an optionally substituted aryl group; $R^1$ represents a hydrogen atom or an optionally substituted alkyl, alkenyl or alkynyl group; $R^2$ represents a hydrogen or halogen atom or an alkyl, haloalkyl, alkoxy, haloalkoxy, alkylthio, hydroxyl, cyano, nitro, amino, alkylamino, dialkylamino or morpholine group; X represents an oxygen or sulphur atom, a carbonyl group or a group —$CR^4R^5$— where $R^4$ and $R^5$ independently represent a hydrogen atom or an alkoxy group; Y represents an oxygen or sulphur atom; n represents an integer from 0 to 6; m is 0 or 1; and Z represents a phenyl group; processes for their preparation; compositions containing such compounds and their use as fungicides.

10 Claims, No Drawings

THIAZOLE DERIVATIVES

This invention relates to certain thiazole derivatives, a process for their preparation, compositions containing such compounds and their use as fungicides.

According to the present invention there is provided a compound of the general formula

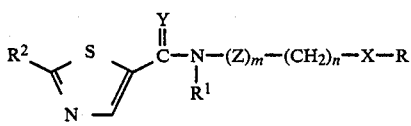 (I)

or an acid-addition salt or metal salt complex thereof, in which R represents an optionally substituted aryl group; $R^1$ represents a hydrogen atom or an optionally substituted alkyl, alkenyl or alkynyl group; $R^2$ represents a hydrogen or halogen atom or an alkyl, haloalkyl, alkoxy, haloalkoxy, alkylthio, hydroxyl, cyano, nitro, amino, alkylamino, dialkylamino or morpholine group; X represents an oxygen or sulphur atom, a carbonyl group or a group $-CR^4R^5-$ where $R^4$ and $R^5$ independently represent a hydrogen atom or an alkoxy group; Y represents an oxygen or sulphur atom; n represents an integer from 0 to 6; m is 0 or 1; and Z represents a phenyl group.

When the compounds of this invention contain an alkyl, alkenyl or alkynyl substituent group, this may be linear or branched and may contain up to 12, preferably up to 8, carbon atoms.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include for example halogen atoms, nitro, cyano, hydroxyl, alkyl, haloalkyl, alkoxy, haloalkoxy, amino, alkylamino, dialkylamino, carbonyl, alkoxycarbonyl, carboxyl, alkanoyl, alkylthio, alkylsulphinyl, alkylsulphonyl, carbamoyl, alkylamido, cycloalkyl and phenyl groups. When any of the foregoing substituents represents or contains an alkyl substituent group, this may be linear or branched and may contain up to 12, preferably up to 6, and especially up to 4, carbon atoms.

Preferably, the aryl group R is a phenyl or naphthyl group. Advantageously, R represents a phenyl group, preferably substituted by 1 to 3 halogen, especially chlorine, atoms.

It is preferred that $R^1$ represents a $C_{1-12}$ alkyl, particularly a $C_{1-8}$ alkyl, group, a $C_{2-12}$ alkenyl, particularly a $C_{2-6}$ alkenyl and especially a $C_{2-4}$ alkenyl group, or a $C_{2-12}$ alkynyl, particularly a $C_{2-6}$ alkynyl and especially a $C_{2-4}$ alkynyl, group, each optionally substituted by one or more substituents selected from halogen atoms, nitro, cyano, hydroxyl, carboxyl, carbonyl, amino, $C_{1-4}$ alkylamino, di-$C_{1-4}$ alkylamino, $C_{1-4}$ alkoxy or haloalkoxy and $C_{1-4}$ alkoxycarbonyl groups.

Preferably, n represents an integer from 0 to 3, especially 2.

A particularly preferred sub-group of compounds of formula I is that in which R represents a mono-, di- or trichlorophenyl, difluorophenyl, tribromophenyl, dichlorofluorophenyl, dichloronitrophenyl, cyanophenyl, propylphenyl, cyclohexylphenyl, biphenylyl or bromonaphthyl group; $R^1$ represents a hydrogen atom or a propyl, butyl, pentyl, hexyl, heptyl, propynyl or methoxyethyl group; $R^2$ represents a hydrogen or chlorine atom or a methoxy, butylthio or morpholine group; X represents an oxygen or sulphur atom, a carbonyl group or a group $-CR^4R^5-$ where $R^4$ and $R^5$ both represent an ethoxy group; Y represents an oxygen or sulphur atom; and n is 0, 2 or 3.

The present invention also provides a process for the preparation of a compound of formula I as defined above which comprises reacting a compound of the general formula

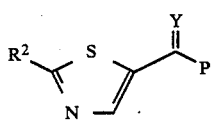 (II)

with a compound of the general formula $$Q-(CH_2)_nXR \quad (III)$$

in which, when m is 0, P represents a group $-NHR^1$ and Q represents a leaving group L or P represents a leaving group L' and Q represents a group $-NHR^1$, when m is 1, P represents a group L' and Q represents a group $-ZNHR^1$, and R, $R^1$, $R^2$, X, Y, n, m and Z have the meanings given above; if desired, reacting resulting compounds of formula I in which Y represents an oxygen atom with a thiating agent to form compounds of formula I in which Y represents a sulphur atom; and, if desired, reacting compounds of formula I with a suitable acid or metal salt to form an acid-addition salt or metal salt complex thereof.

Conveniently, a compound of formula I in which m is 0 is prepared by reacting a compound of formula II in which P is $-NHR^1$ and a compound of formula III in which Q is L in the presence of a suitable base, such as sodium hydroxide, potassium hydroxide, pyridine and, most preferably, butyl lithium. Alternatively, a compound of formula I in which m is 0 or 1 may be prepared by reacting a compound of formula II in which P is L' and a compound of formula III in which Q is $-(Z)_mNHR^1$, advantageously in the presence of a suitable base, such as pyridine.

Suitable thiating agents include Lawesson's Reagent (2,4-bis-(4-methoxyphenyl)-1,3-dithia-2,4-diphosphetane-2,4-disulphide), a known compound which may be prepared according to the method described by S. Scheibyl, B. S. Pedersen and S. O. Lawesson in Bull. Soc. Chim. Belg., 1978, 87, 229.

The leaving group L may conveniently be a chlorine or bromine atom or a group $-OSO_2R^3$ in which $R^3$ represents an optionally substituted $C_{1-4}$ alkyl or aryl group. The leaving group L' may be a chlorine or bromine atom or a hydroxyl or alkoxy group.

In cases where P represents a chlorine or bromine atom, it is preferred that the compound of formula II is generated in situ from the corresponding hydroxyl compound, preferably by treatment with a suitable chlorinating agent such as thionyl chloride or brominating agent such as thionyl bromide, prior to admixture with the compound of formula III.

The process of the invention is conveniently carried out in the presence of a solvent. Suitable solvents include dimethyl sulphoxide, hexamethylphosphoric triamide, ethers, particularly tetrahydrofuran, esters, halogenated hydrocarbons, amines, particularly pyridine, alcohols and aromatic compounds. The reaction is suitably carried out at a temperature of −100° to 150° C., the preferred reaction temperature being −80° to 70° C.

Compounds of formula II in which P represents a group —NHR$^1$ and R$^2$ represents a chlorine atom may conveniently be prepared by reacting 2-chlorothiazole with a compound of the general formula $$R^1N=C=O \qquad (IV)$$

where R$^1$ is as defined above, preferably in the presence of a suitable base, such as butyl lithium. The resulting compounds may then be converted into other compounds of formula II in which R$^2$ does not represent a chlorine atom by means of conventional substitution reactions. For instance, compounds of formula II in which R$^2$ represents a hydrogen atom may be prepared by reacting compounds of formula II in which R$^2$ represents a chlorine atom with a suitable reducing agent, such as zinc in acetic acid.

2-chlorothiazole may be prepared from 2-aminothiazole (a known compound) using the procedure of K. Ganapathi and A. Venkataraman, Proc. Indian Acad. Sci., 1945, 22A, 343, 362. The compounds of formula IV are all known compounds and may be prepared according to processes described in a review of the industrial preparation of isocyanates by Twitchett, Chem. Soc. Rev., 1974, 3, 209.

Compounds of formula II in which P represents a group L' where L' is a chlorine or bromine atom may be prepared by reacting the corresponding hydroxyl compound with thionyl chloride or thionyl bromide as described earlier. Compounds of formula II in which P represents a group L' where L' is a hydroxyl group may conveniently be prepared by treating the corresponding ester with acid. The corresponding esters, that is, compounds of formula II in which P represents a group L' where L' is an alkoxy group, may be prepared by the deamination of the corresponding alkyl-2-aminothiazole-5-carboxylate, the latter being prepared by the method of E. Campaigne and W. L. Archer, J.A.C.S., 1952, 74, 5799.

Compounds of formula III in which Q represents a group —NHR$^1$ may be prepared by reacting a compound of the general formula $$RX(CH_2)_n\,Hal \qquad (V)$$

where R, X and n are as defined above and Hal represents a halogen atom, with an amine of the formula R$^1$NH$_2$, preferably in the presence of a suitable base, such as triethylamine.

Compounds of formula III in which Q represents a group -ZNHR$^1$ are known compounds.

Compounds of formula V (which embrace compounds of formula III in which Q represents a chlorine or bromine atom) may be prepared by reacting a compound of the formula RXH with a suitable haloalkane, preferably in the presence of a suitable base, such as sodium hydroxide.

The haloalkanes, amines R$^1$NH$_2$ and compounds RXH are known compounds or can be prepared by processes analogous to known processes.

Compounds of formula III in which Q represents a group —OSO$_2$R$^3$ are either known compounds or may be prepared by reacting a compound of the general formula $$RX(CH_2)_nOH \qquad (VI)$$

where R, X and n are as defined above, with a compound of the general formula $$R^3SO_2Cl \qquad (VII)$$

where R is as defined above, preferably in the presence of a suitable base, such as triethylamine.

Compounds of formula VI may be prepared by reacting a compound of formula RXH with a suitable alkene carbonate in the presence of tetraethylammonium iodide according to the method of T. Yoshino, S. Inaba and Y. Ishido, Bull. Chem. Soc., Jpn., 1973, 46, 553.

Compounds of formula VII, formula RXH, the alkene carbonates and tetraethylammonium iodide are either known compounds or can be prepared by processes analogous to known processes.

In accordance with another aspect of the invention there is provided a fungicidal composition which comprises a carrier and, as active ingredient, a compound of formula I or an acid-addition salt or metal salt complex thereof as defined above. A method of making such a composition is also provided which comprises bringing a compound of formula I or an acid-addition salt or metal salt complex thereof into association with at least one carrier.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or an acid-addition salt or metal salt complex thereof, and a method for combating fungus at a locus, which comprises treating the locus, which may be for example plants subject to or subjected to fungal attack, seeds of such plants or the medium in which such plants are growing or are to be grown, with such a compound.

The present invention is of wide applicability in the protection of crop plants against fungal attack. Typical crops which may be protected include vines, grain crops such as wheat and barley, rice and tomatoes. The duration of protection is normally dependent on the individual compound selected, and also a variety of external factors, such as climate, whose impact is normally mitigated by the use of a suitable formulation.

The invention is further illustrated by the following Examples.

EXAMPLE 1

(A) Preparation of methyl thiazole-5-carboxylate

Methyl 2-aminothiazole-5-carboxylate (79 g, 0.5 mol) was added over a period of 2 hours to a boiling solution of amyl nitrite (117.0 g, 1.0 mol) in dioxan (1 liter). After refluxing for a further half hour, the solvent was removed under reduced pressure and the residue was steam distilled to give a yellow oil which, on trituration with petroleum ether, gave the desired product as a white solid (32.0 g), m.pt. 68° C.

(B) Preparation of thiazole-5-carboxylic acid

A solution of sodium hydroxide (6.3 g) in water (100 ml) was added to a solution of the methyl thiazole-5-carboxylate (15.0 g, 0.1 mol) obtained in A in ethanol (100 ml). After 10 minutes, the ethanol was removed under reduced pressure and the residue was acidified with hydrochloric acid to pH 1 to give thiazole-5-carboxylic acid as a white solid (12.1 lg), m.pt. 218° C.

(C) Preparation of N-propyl-N-2-(2,4,6-trichlorophenoxy)ethylamine

A solution of sodium hydroxide (7.8 g, 0.195 mol) in water (20 ml) was added to a solution of 2,4,6-trichlorophenol (38.0 g, 0.192 mol) in ethanol (200 ml). 1,2-dibromoethane (47 g, 0.25 mol) was then added and the resultant mixture was refluxed overnight. On cooling, the solid was filtered off and the filtrate concentrated under reduced pressure. Ether was added to the residue and the solution was then washed with dilute sodium hydroxide solution and dried over anhydrous magnesium sulphate. After removal of the solvent by evaporation, the residue was recrystallised from ethanol to give 1-bromo-2-(2,4,6-trichlorophenoxy)ethane as a white solid (39.4 g). A mixture of the 1-bromo-2-(2,4,6-trichlorophenoxy) ethane (20.0 g, 0.066 mol), triethylamine (6.7 g, 0.066 mol) and propylamine (3.9 g, 0.066 mol) in ethanol (500 ml) was then refluxed overnight. After removal of the solvent by evaporation, the residue was dissolved in ether, washed with water and dried (MgSO$_4$). Evaporation of the solvent left an oil which, after flash chromatography on silica gel using chloroform as the eluant, yielded N-propyl-N-2-(2,4,6-trichlorophenoxy)ethylamine as an oil (12.6 g).

(D) Preparation of N-propyl-N-[2-(2,4,6-trichlorophenoxy)ethyl]-thiazole-5-carboxamide The thiazole-5-carboxylic acid (4.8 g, 0.037 mol) obtained in B was refluxed in excess thionyl chloride (100 mls) for 2 hours, cooled and the excess thionyl chloride removed in vacuo. The residue was suspended in dry pyridine (30 mls) and cooled in an ice bath for 10 minutes. A solution of the N-propyl-N-2-(2,4,6-trichlorophenoxy)ethylamine (10.7 g, 0.038 mol) obtained in C in pyridine (60 mls) was added to the cooled suspension dropwise with stirring. The pyridine was then removed by evaporation, the residue taken up in chloroform (250 mls) and washed with water (60 mls). The organic layer was then dried over magnesium sulphate, filtered and the solvent removed to leave a light brown oil which was purified by column chromatography using 75:25 hexane:ethyl acetate as eluant to yield the desired final product as a white solid (8.6 g).

Analysis Calc: C 45.7; H 3.8; N 7.1%:
Found: C 45.6; H 3.9; N 7.2%

EXAMPLE 2

(A) Preparation of N-propyl thiazole-5-carboxamide

Butyl lithium (2.4 M, 50 ml) in hexane was added to a solution of 2-chlorothiazole (12.43 g, 0.104 mol) in tetrahydrofuran (400 ml) at −78° C. under at atmosphere of nitrogen. The resultant solution was stirred for 5 minutes before propyl isocyanate (11.25 ml, 0.12 mol) was added and the reaction mixture was then stirred for a further 10 minutes before being hydrolysed with water (100 ml). The solvent was removed under reduced pressure and the residue extracted with ethyl acetate (2×400 ml). The combined organic extract was then washed with saturated sodium chloride solution, dried over magnesium sulphate and the solvent evaporated. Acetic acid (110 ml) was added to the residue and the solution warmed to about 100° C. whereupon zinc dust (11.8 g) was added and the mixture was refluxed for 1 hour. On cooling, the reaction mixture was made basic with ammonium hydroxide and then extracted into ethyl acetate (4×250 ml). The combined organic extract was washed with saturated sodium chloride solution, dried (MgSO$_4$) and then concentrated. Flash chromatography of the residue on a silica gel column using ethyl acetate as eluant gave N-propylthiazole-5-carboxamide (12.2 g) as a pale yellow solid, m.pt. 86° C.

(B) Preparation of 2-(4-chlorophenoxy)-1-(4-chlorophenylsulphonyl)ethane

A mixture of 4-chlorophenol (28.3 g, 0.22 mol), ethylene carbonate (19.4 g, 0.22 mol) and tetraethylammonium iodide (10 g, 3.6 mmol) was heated at 160° C. for 3 hours and then cooled to room temperature. Chloroform (500 ml) was added and the resultant solution was washed with water and then dried over anhydrous sodium sulphate. Evaporation of the solvent gave 2-(4-chlorophenoxy)ethanol (40.0 g) which was dissolved in ether (400 ml) containing triethylamine (20 g, 0.2 mol) A solution of 4-chlorophenylsulphonyl chloride (42.0 g, 0.2 mol) in ether (150 ml) was added dropwise and the resultant mixture was refluxed for 40 hours and then cooled. The precipitate was filtered off and washed well with dichloromethane. The combined filtrate and washings were dried over anhydrous sodium sulphate. After removal of the solvent by evaporation, the residue was recrystallised from ethyl acetate to give 2-(4-chlorophenoxy)-1-(4-chlorophenylsulphonyl)ethane as a white solid (34.6 g, m.pt. 108° C.

(C) Preparation of N-propyl-N-[2-(4-chlorophenoxy)ethyl]thiazole-5-carboxamide

Butyl lithium (1.6 M, 7.5 ml) in hexane was added to a solution of the N-propyl thiazole-5-carboxamide (1.7 g, 10 mmol) obtained in A in tetrahydrofuran (80 ml) at −78° C. under an atmosphere of nitrogen. The resultant solution was stirred for 10 minutes and then allowed to warm to room temperature whereupon the 2-(4-chlorophenoxy)-1-(4-chlorophenylsulphonyl)ethane (5.20 g, 15 mmol) obtained in B dissolved in tetrahydrofuran (40 ml) was added. The resultant solution was then refluxed for 5 days. On cooling, the solvent was evaporated and the residue dissolved in 1:4 water: ethyl acetate (500 ml). The organic layer was washed with saturated sodium chloride solution, dried (MgSO$_4$) and the solvent evaporated to leave an oil which, after flash chromatography on silica gel with 1:2 ethylacetate: petroleum ether as the eluant, yielded the desired product (2.42 g). Mass spectroscopy revealed the mass/charge ratio of the parent molecule ion, M$^+$, to be 324 thereby confirming the molecular weight of the product to be 324.

EXAMPLE 3

Preparation of N-propyl-N-[2-(4-chlorophenoxy)ethyl]-thiazole-5-thiocarboxamide

A mixture of the N-propyl-N-[2-(4-chlorophenoxy)ethyl]thiazole-5-carboxamide (0.9 g, 3 mmol) obtained in Example 2B and Lawesson's Reagent (2,4-bis(4-methoxyphenyl)-1,3-dithia-2,4-diphosphetane-2,4-disulphide, 1.2g, 3 mmol) was refluxed for 20 hours and then cooled to room temperature. Water (100 ml) was added and the residue was extracted into ether (2×200 ml). The combined organic extract was washed with saturated sodium chloride solution (50 ml) and dried over magnesium sulphate. Evaporation of the solvent left an oil which, after flash chromatography on silica gel using 1:1 ethyl acetate: petroleum ether as the eluant, yielded the desired product as a yellow oil (0.75 g), M$^+$ found: 340

EXAMPLES 4 to 43

By processes similar to those described in Examples 1 to 3 above, further compounds according to the present invention were prepared as detailed in Table I below. In this table, the compounds are identified by reference to formula I. The characterising data for these compounds is set out in Table IA.

TABLE I

| Example No. | R | R¹ | R² | X | Y | n | m | Z |
|---|---|---|---|---|---|---|---|---|
| 4 | 4-chlorophenyl | (CH₃)₂CH— | H | O | O | 2 | 0 | — |
| 5 | 2,4-dichlorophenyl | CH₃CH₂CH₂— | H | O | O | 2 | 0 | — |
| 6 | 2,4-dichlorophenyl | CH₃CH₂CH₂— | H | O | S | 2 | 0 | — |
| 7 | 2,4-dichlorophenyl | CH₃CH₂CH₂CH₂— | H | O | O | 2 | 0 | — |
| 8 | 2,4-dichlorophenyl | CH₃CH₂CH₂CH₂CH₂— | H | O | O | 2 | 0 | — |
| 9 | 2,4,6-trichlorophenyl | (CH₃)₂CH— | H | O | O | 2 | 0 | — |
| 10 | 2,4,6-trichlorophenyl | CH₃CH₂CH₂— | H | O | O | 2 | 0 | — |
| 11 | 2,4,6-trichlorophenyl | (CH₃)₂CHCH₂— | H | O | O | 2 | 0 | — |
| 12 | 2,4,6-trichlorophenyl | (C₂H₅)(CH₃)CH— | H | O | O | 2 | 0 | — |
| 13 | 2,4,6-trichlorophenyl | (CH₃)₃C— | H | O | O | 2 | 0 | — |
| 14 | 2,4,6-trichlorophenyl | CH₃CH₂CH₂CH₂— | H | O | O | 2 | 0 | — |
| 15 | 2,4,6-trichlorophenyl | (C₂H₅)(CH₃)₂C— | H | O | O | 2 | 0 | — |
| 16 | 2,4,6-trichlorophenyl | CH₃CH₂CH₂CH₂CH₂— | H | O | O | 2 | 0 | — |
| 17 | 2,4,6-trichlorophenyl | CH₃CH₂CH₂CH₂CH₂CH₂CH₂— | H | O | O | 2 | 0 | — |
| 18 | 2,4,6-trichlorophenyl | CH≡C—CH₂— | H | O | O | 2 | 0 | — |
| 19 | 2,4,6-trichlorophenyl | CH₃OCH₂CH₂— | H | O | O | 2 | 0 | — |
| 20 | 2,4-difluorophenyl | CH₃CH₂CH₂— | H | O | O | 2 | 0 | — |
| 21 | 2,4,6-trichlorophenyl | CH₃CH₂CH₂— | H | O | O | 3 | 0 | — |
| 22 | 2,4,6-trichlorophenyl | H— | H | O | O | 2 | 0 | — |
| 23 | 2,4-dichlorophenyl | CH₃CH₂CH₂CH₂CH₂— | H | O | O | 2 | 0 | — |
| 24 | 2,4-dichlorophenyl | CH₃CH₂CH₂CH₂CH₂CH₂— | H | O | O | 2 | 0 | — |
| 25 | 4-chlorophenyl | H— | H | —CO— | O | 0 | 1 |  |
| 26 | 2,6-dichloro-4-nitrophenyl | CH₃CH₂CH₂— | H | O | O | 2 | 0 | — |
| 27 | 2,4,6-tribromophenyl | CH₃CH₂CH₂— | H | O | O | 2 | 0 | — |
| 28 | 2,6-dichloro-4-fluorophenyl | CH₃CH₂CH₂— | H | O | O | 2 | 0 | — |
| 29 | 2,4-difluorophenyl | CH₃OCH₂CH₂— | H | O | O | 2 | 0 | — |
| 30 | 3,4-dichlorophenyl | CH₃CH₂CH₂— | H | O | O | 2 | 0 | — |
| 31 | 3,5-dichlorophenyl | CH₃CH₂CH₂— | H | O | O | 2 | 0 | — |
| 32 | 2,4-difluorophenyl | CH₃CH₂CH₂CH₂CH₂— | H | O | O | 2 | 0 | — |
| 33 | 4-chlorophenyl | H— | H | —C(OC₂H₅)₂— | O | 0 | 1 |  |
| 34 | 4-n-propylphenyl | CH₃CH₂CH₂— | H | O | O | 2 | 0 | — |
| 35 | 2-biphenylyl | CH₃CH₂CH₂— | H | O | O | 2 | 0 | — |
| 36 | 4-cyanophenyl | CH₃CH₂CH₂— | H | O | O | 2 | 0 | — |
| 37 | 4-cyclohexylphenyl | CH₃CH₂CH₂— | H | O | O | 2 | 0 | — |
| 38 | 6-bromonaphth-2-yl | CH₃CH₂CH₂— | H | O | O | 2 | 0 | — |
| 39 | 2,4,6-trichlorophenyl | CH₃CH₂CH₂— | Cl | O | O | 2 | 0 | — |
| 40 | 4-chlorophenyl | CH₃CH₂CH₂— | H | S | O | 2 | 0 | — |
| 41 | 2,4,6-trichlorophenyl | CH₃CH₂CH₂ | (CH₃)₂CHCH₂S— | O | O | 2 | 0 | — |
| 42 | 2,4,6-trichlorophenyl | CH₃CH₂CH₂— | CH₃O— | O | O | 2 | 0 | — |
| 43 | 2,4,6-trichlorophenyl | CH₃CH₂CH₂— | —N O | O | O | 2 | 0 | — |

TABLE IA

| Example No. | m.pt °C. | M⁺ found | C Calc. | C Found | H Calc. | H Found | N Calc. | N Found |
|---|---|---|---|---|---|---|---|---|
| 4 | — | 324 | | | | | | |
| 5 | — | 358 | 50.3 | 50.5 | 4.5 | 4.6 | 7.8 | 7.8 |
| 6 | — | 374 | 48.1 | 48.5 | 4.3 | 4.6 | 7.5 | 8.0 |
| 7 | — | 372 | 51.6 | 51.3 | 4.8 | 4.2 | 7.5 | 7.9 |
| 8 | — | 386 | 52.8 | 52.3 | 5.2 | 5.6 | 7.3 | 7.5 |
| 9 | — | 392 | 45.9 | 44.9 | 3.8 | 3.8 | 7.1 | 7.1 |
| 10 | — | 406 | 47.3 | 46.9 | 4.2 | 4.1 | 6.9 | 7.2 |
| 11 | — | 406 | 47.3 | 46.9 | 4.2 | 4.3 | 6.9 | 6.3 |
| 12 | — | 406 | 47.3 | 46.5 | 4.2 | 4.1 | 6.9 | 6.3 |
| 13 | — | 406 | 47.3 | 46.0 | 4.2 | 4.0 | 6.9 | 6.6 |
| 14 | — | 420 | 48.6 | 48.9 | 4.5 | 4.5 | 6.7 | 6.7 |
| 15 | — | 420 | 48.6 | 49.2 | 4.5 | 4.6 | 6.7 | 7.3 |
| 16 | — | 434 | 49.8 | 49.6 | 4.8 | 3.2 | 6.5 | 6.9 |
| 17 | — | 448 | 50.8 | 50.9 | 5.1 | 5.8 | 6.3 | 6.8 |
| 18 | — | 388 | 46.2 | 45.3 | 2.8 | 2.5 | 7.2 | 7.5 |
| 19 | — | 408 | 44.0 | 43.8 | 3.7 | 3.8 | 6.8 | 6.8 |
| 20 | — | 326 | 55.2 | 55.0 | 4.9 | 3.5 | 8.6 | 9.1 |
| 21 | — | — | 47.12 | 48.05 | 4.17 | 4.35 | 6.87 | 6.90 |
| 22 | 104–5 | — | 40.97 | 42.05 | 2.56 | 2.75 | 7.97 | 7.85 |
| 23 | 48–9 | — | 52.71 | 52.75 | 5.17 | 5.50 | 7.24 | 6.95 |
| 24 | 57–9 | — | 53.87 | 52.05 | 5.49 | 5.25 | 6.98 | 7.05 |
| 25 | 168–9 | — | 59.56 | 59.0 | 3.21 | 3.55 | 8.18 | 8.35 |
| 26 | oil | — | 44.55 | | 3.71 | | 10.4 | |
| 27 | — | — | 34.16 | 33.90 | 2.85 | 2.70 | 5.31 | 5.80 |
| 28 | — | — | 47.75 | 47.90 | 3.98 | 4.15 | 7.43 | 7.50 |
| 29 | — | — | 52.63 | 52.85 | 4.68 | 4.90 | 8.19 | 8.20 |
| 30 | — | — | 50.14 | 50.30 | 4.46 | 4.60 | 7.80 | 8.10 |
| 31 | — | — | 50.14 | 49.95 | 4.46 | 4.60 | 7.80 | 7.80 |
| 32 | — | — | 57.63 | 58.10 | 5.65 | 5.90 | 7.91 | 7.90 |
| 33 | — | — | 60.50 | 56.65 | 5.04 | 5.05 | 6.72 | 6.65 |
| 34 | — | — | 65.06 | 64.30 | 7.23 | 7.35 | 8.43 | 8.30 |
| 35 | — | — | 68.85 | 67.95 | 6.01 | 6.15 | 7.65 | 7.85 |
| 36 | 60–1 | — | 60.95 | 60.50 | 5.40 | 5.25 | 13.33 | 13.10 |
| 37 | — | — | 67.74 | 65.3 | 7.53 | 7.10 | 7.53 | 7.15 |
| 38 | 83–4 | — | 54.42 | 53.05 | 4.53 | 4.25 | 6.68 | 6.50 |
| 39 | — | — | 42.06 | 42.30 | 3.27 | 3.50 | 6.54 | 6.50 |
| 40 | — | — | 52.86 | 52.55 | 4.99 | 5.00 | 8.22 | 8.35 |
| 41 | — | — | 47.35 | 46.90 | 4.78 | 4.80 | 5.82 | 6.10 |
| 42 | 136–7 | — | 45.34 | 43.10 | 4.01 | 3.20 | 6.61 | 6.25 |

TABLE IA-continued

| Example No. | m.pt °C. | M+ found | Analysis | | | | | |
|---|---|---|---|---|---|---|---|---|
| | | | C | | H | | N | |
| | | | Calc. | Found | Calc. | Found | Calc. | Found |
| 43 | 131-2 | — | 47.65 | 47.3 | 4.60 | 4.65 | 8.78 | 8.55 |

EXAMPLE 44

The fungicidal activity of compounds of the invention was investigated by means of the following tests.

(a) Antisporulant activity against vine downy mildew (*Plasmopara viticola*; Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN" 20 (Trade Mark; a polyoxyethylene sorbitan ester surfactant). The spraying is carried out with a moving track sprayer giving an application rate of 1 kg/ha. After spraying, the plants are returned to normal glasshouse conditions for 96 hours and are then transferred to the high humidity compartment for 24 hours to induce sporulation, prior to assessment. Assessment is based on the percentage of the leaf area covered by sporulation compared with that on control leaves.

(b) Direct protectant activity against vine downy mildew *Plasmopara viticola*; Pvp)

The test is a direct protectant one using a foliar spray. The lower surfaces of leaves of whole vine plants (cv Cabernet Sauvignon) are sprayed with the test compound at a dosage of 1 kilogram of active material per hectare using a track sprayer as described under (a), and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(c) Direct protectant activity against vine grey mould (*Botrytis cinerea*; Bcp)

The test is a direct protectant one using a foliar spray. The lower surfaces of detached vine leaves (cv Cabernet Sauvignon) are sprayed with the test compound at a dosage of 1 kg/ha using a track sprayer as in (a). 24 hours after spraying the leaves are inoculated with droplets of aqueous suspension containing $10^5$ conidia/ml. After a further 5 days in high humidity the percentage of leaf area covered by disease is assessed.

(d) Activity against wheat leafspot (*Leptosphaeria nodorum*; Ln.)

The test is a direct therapeutic one, using a foliar spray. Leaves of wheat plants (cv Mardler), at the single leaf stage, are inoculated by spraying with an aqueous suspension containing $1 \times 10^6$ spores/ml. The inoculated plants are kept for 24 hours in a high humidity compartment prior to treatment. The plants are sprayed with a solution of the test compound at a dosage of 1 kilogram of active material per hectare using a track sprayer as described under (a). After drying, the plants are kept for 6-8 days at 20°-25° C. and moderate humidity, followed by assessment. Assessment is based on the density of lesions per leaf compared with that on leaves of control plants.

(e) Activity against barley powdery mildew (*Erysiphe graminis* f.sp. hordei; Eg)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1 kilogram of active material per hectare using a track sprayer as described under (a). After drying, plants are returned to a compartment at 20°-25° C. and moderate humidity for up to 7 days, followed by assessment. Assessment is based on the percentage of leaf area covered by sporulation compared with that on leaves of control plants.

(f) Activity against wheat brown rust (*Puccinia recondita*; Pr)

The test is a direct protectant one using a foliar spray. Wheat seedings (cv Brigand) are grown to the 1-1½ leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20"-Trade Mark).

18-24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°-22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

(g) Activity against rice leaf blast (*Pyricularia oryzae* Po)

The test is a direct therapeutic one using a foliar spray. The leaves of rice seedlings (about 30 seedlings per pot) are sprayed with an aqueous suspension containing $10^5$ spores/ml 20-24 hours prior to treatment with the test compound. The inoculated plants are kept overnight in high humidity and then allowed to dry before spraying with the test compound at a dosage of 1 kilogram of active material per hectare using a track sprayer as described under (a). After treatment the plants are kept in a rice compartment at 25°-30° C. and high humidity. Assessments are made 4-5 days after treatment and are based on the density of necrotic lesions per leaf when compared with control plants.

(h) Activity against tomato early blight (*Alternaria solani*; As)

This test measures the contact prophylactic activity of test compounds applied as a foliar spray.

Tomato seedlings (cv Outdoor Girl) are grown to the stage at which the second true leaf is expanded. The plants are treated using a track sprayer as described under (a). Test compounds are applied as solutions or suspensions in a mixture of acetone and water (50:50 v/v) containing 0.04% surfactant ("TWEEN 20"-Trade mark).

One day after treatment the seedlings are inoculated by spraying the leaf upper surfaces with a suspension of *A. solani* conidia containing $10^4$ spores/ml. For 3 days after inoculation plants are kept moist in a glasshouse compartment at or near 100% RH and 21° C. Thereafter plants are kept under humid, but not saturated, conditions.

Disease is assessed 7 days after inoculation, based on the density and spread of lesions.

(i) Activity against wheat eyespot in-vitro (*Pseudocercosporella herpotrichoides*; PhI)

This test measures the in vitro activity of compounds against the fungus causing wheat eyespot.

The test compound is dissolved or suspended in acetone and is added to molten half strength Potato Dextrose Agar to give a final concentration of 100 ppm compound and 3.5% acetone. After agar has set, plates are inoculated with 6 mm diameter plugs of agar/mycelium taken from a 14 day old culture of *P. herpotrichoides*.

Plates are incubated at 20° C. for 12 days and radial growth from the inoculation plug is measured.

(j) Activity against Fusarium in-vitro (*Fusarium species*; FsI)

This test measures the in vitro activity of compounds against a species of Fusarium that causes stem and root rots.

Compound is dissolved or suspended in acetone and added to molten half strength Potato Dextrose Agar to give a final concentration of 100 ppm compound and 3.5% acetone. After agar has set, plates are inoculated with 6 mm diameter plugs of agar and mycelium taken from a 7 day old culture of Fusarium sp.

Plates are incubated at 20° C. for 5 days and radial growth from the plug is measured.

The extent of disease control in all the above tests is expressed as a rating compared with either an untreated control or a diluent-sprayed-control, according to the criteria:

0 = less than 50% disease control
1 = about 50–80% disease control
2 = greater than 80% disease control The results of these tests are set out in Table II below:

TABLE II

| Compound Example No. | Fungicidal Activity | | | | | | | | | |
|---|---|---|---|---|---|---|---|---|---|---|
| | Pva | Pvp | Bcp | Ln | Eg | Pr | Po | As | PhI | FsI |
| 1 | | 1 | | 2 | 2 | 1 | 2 | 2 | 2 | 2 |
| 2 | | 1 | | 2 | 2 | | 2 | 2 | 1 | 2 |
| 3 | 1 | | 1 | 2 | 2 | 1 | | 2 | 1 | 1 |
| 4 | | | | 2 | 2 | 1 | 1 | 1 | 1 | 2 |
| 5 | | 2 | | 2 | 2 | | | 1 | | 1 |
| 6 | 1 | | | 2 | 2 | 1 | 1 | 1 | 1 | 1 |
| 7 | | 2 | | 2 | 2 | 1 | 1 | | 1 | 1 |
| 8 | | | | 2 | 2 | | | | 1 | 1 |
| 9 | | | | 1 | 1 | | | | 1 | 1 |
| 10 | | 1 | | 2 | 2 | 1 | 2 | 1 | 1 | 2 |
| 11 | | | | 2 | 2 | 1 | 1 | | 2 | 1 |
| 12 | | 1 | | 1 | 2 | 1 | 2 | | 1 | 1 |
| 13 | | 1 | | 1 | 2 | 1 | | | | 1 |
| 14 | | | | 2 | 2 | | 1 | 2 | 1 | 1 |
| 15 | | | | 2 | 2 | | | | | |
| 16 | | 2 | | 2 | 2 | | 1 | 1 | 1 | 1 |
| 17 | | | | 2 | 2 | | 1 | 1 | 1 | |
| 18 | | 1 | | 2 | 2 | 1 | | 1 | 1 | 2 |
| 19 | | | | 2 | 2 | 1 | 2 | 1 | 1 | 2 |
| 20 | | | | 2 | 2 | | 2 | 1 | 1 | 1 |
| 21 | 1 | | | 2 | 2 | | | | | 1 |

TABLE II-continued

| Compound Example No. | Fungicidal Activity | | | | | | | | | |
|---|---|---|---|---|---|---|---|---|---|---|
| | Pva | Pvp | Bcp | Ln | Eg | Pr | Po | As | PhI | FsI |
| 22 | 1 | 2 | | | 2 | 2 | 2 | | 1 | 1 |
| 23 | 1 | | | | 2 | 2 | 1 | 2 | 1 | |
| 24 | | | | | 1 | 2 | | | 1 | |
| 25 | | | | | | 2 | | | | |
| 26 | | | | | | 1 | | | | |
| 27 | | 1 | | | 2 | 2 | | 2 | 1 | 1 | 2 |
| 28 | | 1 | | | 2 | 2 | | 2 | 2 | 2 | 2 |
| 29 | | 1 | | | 1 | 2 | 1 | | | | 1 |
| 30 | | 1 | | | 2 | 2 | | 1 | 1 | 1 | 1 |
| 31 | | 1 | | | 2 | 2 | | | | | 1 |
| 32 | | 1 | | | 2 | 2 | | 1 | 1 | 1 | |
| 33 | | 1 | | | 1 | 2 | | 1 | | | |
| 34 | | | | | 2 | 2 | | 2 | 1 | | 1 |
| 35 | | 1 | | | 2 | 2 | 1 | | | | 1 |
| 36 | | 1 | | | | 2 | | 2 | 1 | | 1 |
| 37 | | | | | | 2 | | | | 1 | 1 |
| 38 | | 1 | | | 2 | 2 | | 2 | | | |
| 39 | | 1 | | | 1 | 2 | | | | | |
| 40 | | 1 | | | 2 | 2 | 1 | | | | 1 |
| 41 | | | | | 2 | 2 | 1 | | | | |
| 42 | 1 | | | | 1 | | | | | 1 |
| 43 | | | | | | 1 | | | | |

We claim:

1. A compound of the general formula:

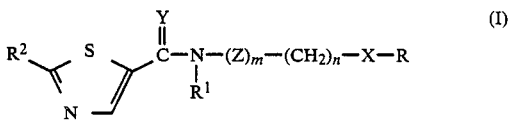

(I)

or an acid-addition salt thereof, in which R represents a phenyl or naphthyl group optionally substituted by one or more substituents selected from the group consisting of halogen atoms, nitro, cyano, hydroxyl, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, carbonyl, $C_{1-6}$ alkoxycarbonyl, carboxyl, $C_{1-6}$ alkanoyl, $C_{1-6}$ alkylthio, $C_{1-6}$ alkylsulfinyl, $C_{1-6}$ alkylsulfonyl, carbamoyl, $C_{1-6}$ alkylamido, $C_{3-6}$ cycloalkyl, and phenyl groups; $R^1$ represents a hydrogen atom or a $C_{1-8}$ alkyl group, a $C_{2-6}$ alkenyl group or a $C_{2-6}$ alkynyl group, each of said alkyl, alkenyl or alkynyl groups being optionally substituted by one or more substituents selected from the group consisting of halogen atoms, nitro, cyano, hydroxyl, carboxyl, carbonyl, amino, $C_{1-4}$ alkylamino, di-$C_{1-4}$ alkylamino, $C_{1-4}$ alkoxy or haloalkoxy and $C_{1-4}$ alkoxycarbonyl groups; $R^2$ represents a hydrogen or halogen atom or a $C_{1-8}$ alkyl, $C_{1-8}$ haloalkyl, $C_{1-8}$ alkoxy, $C_{1-8}$ haloalkoxy, $C_{1-8}$ alkylthio, hydroxyl, cyano, nitro, amino, $C_{1-8}$ alkylamino, di-$C_{1-8}$ alkylamino or morpholine group; X represents an oxygen or sulfur atom, a carbonyl group or a group $—CR^4R^5—$ where $R^4$ and $R^5$ independently represent a hydrogen atom or a $C_{1-8}$ alkoxy group: Y represents an oxygen or sulfur atom; n represents an integer from 0 to 6; m is 0 or 1; and Z represents a phenyl group; with the proviso that m and n do not simultaneously represent 0.

2. A compound according to claim 1 in which R represents a phenyl group substituted by 1 to 3 halogen atoms.

3. A compound according to claim 2 in which the halogen atoms are chlorine atoms.

4. A compound according to claim 1 in which R represents a mono-, di- or trichlorophenyl, difluorophenyl, tribromophenyl, dichlorofluorophenyl, dichloronitrophenyl, cyanophenyl, propylphenyl, cyclohexylphenyl, biphenylyl or bromonaphthyl group; $R^1$ represents a hydrogen atom or a propyl, butyl, pentyl, hexyl, heptyl, propynyl or methoxyethyl group; $R^2$ represents a hydrogen or chlorine atom or a methoxy, butylthio or morpholine group; X represents an oxygen or sulphur atom, a carbonyl group or a group —$CR^4R^5$— where $R^4$ and $R^5$ both represent an ethoxy group; Y represents an oxygen or sulphur atom; and n is 0, 2 or 3.

5. A compound according to claim 4 in which R represents a mono-, di- or trichlorophenyl, difluorophenyl, tribromophenyl, dichlorofluorophenyl or bromonaphthyl group.

6. A compound according to claim 1 in which R represents a mono-, di-, or trichlorophenyl.

7. A fungicidal composition which comprises a carrier and, as active ingredient, a compound of formula I or an acid-addition salt thereof as defined in claim 1.

8. A composition according to claim 7 which comprises at least two carriers, at least one of which is surface-active agent.

9. A method of combating fungus at a locus whi comprises treating the locus with a compound of fo. mula I as defined in claim 1.

10. A method according to claim 9 in which the locus comprises plants subject to or subjected to fungal attack, seeds of such plants or the medium in which the plants are growing or are to be grown.

* * * * *